(12) United States Patent
Cho et al.

(10) Patent No.: US 12,303,111 B2
(45) Date of Patent: May 20, 2025

(54) THREE-DIMENSIONAL SCANNER

(71) Applicant: MEDIT CORP., Seoul (KR)

(72) Inventors: Eun Gil Cho, Seoul (KR); Kwang Jin Jang, Seoul (KR)

(73) Assignee: MEDIT CORP., Seoul (KR)

( * ) Notice: Subject to any disclaimer, the term of this patent is extended or adjusted under 35 U.S.C. 154(b) by 13 days.

(21) Appl. No.: 18/272,763

(22) PCT Filed: Jan. 17, 2022

(86) PCT No.: PCT/KR2022/000828
§ 371 (c)(1),
(2) Date: Jul. 17, 2023

(87) PCT Pub. No.: WO2022/154622
PCT Pub. Date: Jul. 21, 2022

(65) Prior Publication Data
US 2024/0098240 A1 Mar. 21, 2024

(30) Foreign Application Priority Data

Jan. 18, 2021 (KR) .................. 10-2021-0006854
Dec. 24, 2021 (KR) .................. 10-2021-0187627

(51) Int. Cl.
*A61B 1/247* (2006.01)
*A61B 1/00* (2006.01)
(Continued)

(52) U.S. Cl.
CPC .......... *A61B 1/247* (2013.01); *A61B 1/00172* (2013.01); *A61B 1/00179* (2013.01);
(Continued)

(58) Field of Classification Search
CPC .......... A61B 1/247; A61B 1/24; A61B 1/0623
See application file for complete search history.

(56) References Cited

U.S. PATENT DOCUMENTS

2005/0090749 A1* 4/2005 Rubbert ............. H04N 1/00026
348/66
2006/0082764 A1 4/2006 Sottery et al.
(Continued)

FOREIGN PATENT DOCUMENTS

CA 2919728 A1 * 7/2017 ......... A61B 1/00009
JP 2006-081842 A 3/2006
(Continued)

OTHER PUBLICATIONS

WIPO Int'l Bureau, English-language translation of Written Opinion for PCT/KR2022/000828 (Jul. 4, 2023) (Year: 2023).*
(Continued)

*Primary Examiner* — David N Werner
(74) *Attorney, Agent, or Firm* — Sughrue Mion, PLLC

(57) ABSTRACT

A three-dimensional scanner according to the present invention comprises: a camera arranged to receive incident light; an optical projector which is arranged on one side of the camera and irradiates light to an object; and a polarization filter which is spaced a certain set distance from the front surface of the camera, wherein the polarization filter is formed to be inclined by a certain set angle with respect to a plane that is perpendicular to an optical path of the light irradiated from the optical projector, so that at least some of the light irradiated from the optical projector passes through the polarization filter and the remaining light is reflected by the surface of the polarization filter and proceeds to outside of the lens of the camera.

7 Claims, 9 Drawing Sheets

(51) Int. Cl.
*A61B 1/06* (2006.01)
*A61B 1/24* (2006.01)
*H04N 13/239* (2018.01)
*H04N 13/254* (2018.01)
*A61C 9/00* (2006.01)

(52) U.S. Cl.
CPC ........ *A61B 1/00186* (2013.01); *A61B 1/0623* (2013.01); *A61B 1/24* (2013.01); *H04N 13/239* (2018.05); *H04N 13/254* (2018.05); *A61C 9/0053* (2013.01)

(56) References Cited

U.S. PATENT DOCUMENTS

| | | | | |
|---|---|---|---|---|
| 2010/0157019 | A1* | 6/2010 | Schwotzer | A61B 5/0084 348/46 |
| 2010/0268069 | A1* | 10/2010 | Liang | A61B 5/1079 600/425 |
| 2010/0311005 | A1 | 12/2010 | Liang | |
| 2013/0189641 | A1* | 7/2013 | Perfect | A61B 1/247 433/29 |
| 2014/0015928 | A1* | 1/2014 | Koinig | G03B 35/08 348/45 |
| 2017/0340197 | A1* | 11/2017 | Elazar | A61B 5/002 |
| 2018/0098691 | A1* | 4/2018 | Wang | A61B 5/4547 |
| 2018/0192877 | A1* | 7/2018 | Atiya | A61C 9/0066 |
| 2019/0388195 | A1* | 12/2019 | Hu | A61B 1/0623 |
| 2020/0170497 | A1 | 6/2020 | Chang et al. | |
| 2021/0045637 | A1 | 2/2021 | Chang et al. | |
| 2021/0093178 | A1* | 4/2021 | Long | A61B 1/247 |
| 2022/0079426 | A1* | 3/2022 | Christiansen | A61B 1/00142 |
| 2023/0068812 | A1* | 3/2023 | Chang | A61B 1/044 |
| 2024/0004175 | A1* | 1/2024 | Christiansen | G02B 5/3083 |
| 2024/0090772 | A1* | 3/2024 | Subhash | A61B 1/000094 |

FOREIGN PATENT DOCUMENTS

| | | |
|---|---|---|
| KR | 10-2007-0098789 A | 10/2007 |
| KR | 10-2018-0057447 A | 5/2018 |
| KR | 10-1874547 B1 | 7/2018 |
| KR | 10-2020-0064922 A | 6/2020 |
| KR | 10-2020-0134145 A | 12/2020 |

OTHER PUBLICATIONS

International Search Report for PCT/KR2022/000828 dated Apr. 29, 2022 [PCT/ISA/210].
Korean Office Action dated Aug. 10, 2023 in Application No. 10-2021-0187627.
Extended European Search Report dated Nov. 26, 2024 from the European Patent Office in Application No. 22739814.6.

* cited by examiner

THREE-DIMENSIONAL SCANNER

TECHNICAL FIELD

The present disclosure relates to a three-dimensional ("3D") scanner and, more particularly, to a 3D scanner capable of easily obtaining a 3D model representing an object.

BACKGROUND 3D scanners are widely used in the field of dental treatment, and users of 3D scanners may easily obtain a 3D model of an object by using a CAD/CAM technology to establish a treatment plan. In addition, a prosthetic treatment product manufacturer in a dental laboratory may easily design and manufacture a prosthetic treatment product based on the obtained 3D model.

Meanwhile, when an object measured by a 3D scanner is a translucent object, light reflected from inside of the object in addition to light reflected from a surface of the object may be received by a camera. When the light reflected from the inside of the object is received by the camera, there is a risk of deterioration in the clarity of image data for generating a 3D model.

The above-mentioned problem will be described in more detail with reference to FIGS. 1A and 1B. FIGS. 1A and 1B show a schematic view illustrating obtaining 3D information by using a 3D scanner and a schematic view illustrating applying a polarizing filter. In a method that is commonly used to form a 3D scanning model of a tooth in an oral cavity by using a 3D scanner, as illustrated in FIG. TA, structured light is projected onto a tooth, which is an object O, light reflected from the tooth is obtained, and a 3D model is obtained from the obtained light.

That is, the light generated from a light generator 170 passes through a projection lens 171, is reflected from inside of the oral cavity including the tooth which is the object O, and then enters inside by passing through a camera lens 121 so that a 3D model is obtained via an imaging sensor 130.

In order to obtain precise surface data of a tooth in a 3D model in this way, it is important to accurately project structured light onto a surface of the tooth, which is an object O, and obtain it. However, in the case of an inner reflection material like a tooth, which is not a surface reflection material that reflects projected light from a surface such as a plaster model, there is a technical problem in that an accurate 3D model cannot be obtained since light projected to the object is not only reflected from the surface of the object, but also transmitted into inside of the material of the object and reflected from the same.

In order to solve this problem, methods for obtaining light reflected only from a surface of an internal reflection material of an object by using optical wave characteristics (e.g., a method using a polarizing filter) are being researched and developed. However, even when a polarizing filter is used, it is difficult to apply the polarizing filter due to precise axis adjustment to prevent loss of 3D data and a surface reflection problem of the polarizing filter itself.

In addition, even when a polarizing plate is applied, as illustrated in FIG. 1B, it is necessary to provide a first polarizing plate 180a in a projection path before light from the light generator 170 is projected onto the object O and to provide a second polarizing plate 180b in an incident path before the light reflected from the object O is incident on the camera lens 121, which means that at least two polarizing plates 180a and 180b should be provided in the case of a single camera and further means that at least three polarizers should be provided in the case where a stereo vision method is applied. Thus, a slim design of the overall product becomes very difficult.

Therefore, in order to obtain clear image data, a single polarizing filter capable of commonly covering the light projection lens 171 and the camera lens 121 is used to block the light reflected from inside of an object from being received into the camera. However, new problems may occur even when such a polarizing filter is used.

A first problem may occur due to a property in which a part of the light being incident on the surface of the polarizing filter is reflected. Some of the light generated from the light projector may not pass through the polarizing filter and may be reflected from the surface of the polarizing filter, and when the light reflected from the surface of the polarizing filter is received by the camera, a so-called "ghost image" in which a form of the light source appears as an afterimage in image data may be generated. The ghost image may obscure surface data representing the object and prevent a user from obtaining a precise 3D model.

A second problem may occur due to the conventional arrangement position of the conventional polarizing filter. More specifically, the conventional polarizing filter is inserted and coupled into a 3D scanner. Accordingly, it is not easy to clean (maintain/repair) the polarizing filter to remove contamination occurring on the polarizing filter.

Accordingly, there is a need for a structure of a 3D scanner to solve problems including the above-mentioned problems of ghost image generation and difficulty in maintenance/repair of a polarizing filter.

SUMMARY

In order to solve the above-mentioned problems, the present disclosure provides a 3D scanner including a polarizing filter disposed at a predetermined distance from a front surface of a camera.

In addition, the present disclosure provides a 3D scanner in which the polarizing filter is disposed to be inclined by a predetermined set angle.

In addition, the present disclosure provides a 3D scanner in which the polarizing filter is exposed to outside under specific conditions.

The technical problems of the present disclosure are not limited to the technical problems mentioned above, and other technical problems not mentioned above will be clearly understood by a person of ordinary skill in the art from the description below.

In order to accomplish purposes as mentioned above, a 3D scanner according to the present disclosure may include: a camera disposed to receive incident light; a light projector disposed on one side of the camera to emit light to an object; and a polarizing filter disposed apart from a front surface of the camera by a predetermined distance, wherein the polarizing filter is disposed to be inclined by a predetermined set angle with respect to a plane perpendicular to a light path of the light emitted by the light projector, such that at least some of the light emitted by the light projector passes through the polarizing filter, and some of a remainder of the light is reflected from a surface of the polarizing filter and travels to outside of a lens of the camera.

In addition, the 3D scanner according to the present disclosure may further include various additional components including the above-described components.

According to the above-described technical solution and the following detailed description, by using the 3D scanner according to the present disclosure, a user can obtain clear image data while minimizing the occurrence of a ghost image, thereby obtaining an accurate 3D model.

In addition, when the 3D scanner according to the present disclosure is used, it is easy to maintain/repair the polarizing filter because the polarizing filter is disposed at a predetermined distance in front of the camera and one surface of the polarizing filter is entirely exposed.

BRIEF DESCRIPTION OF DRAWINGS

FIG. 6 is viewed from the top.

[Description of Reference Numerals]

Figure 1A:
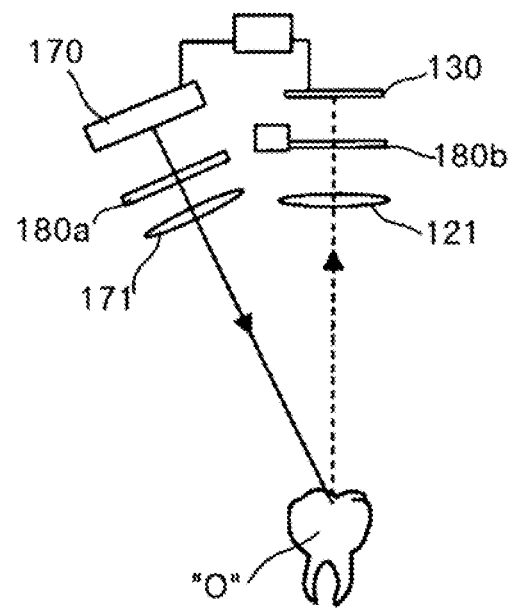
FIGS. 1A and 1B show a schematic view illustrating obtaining 3D information by using a 3D scanner and a schematic view illustrating applying a polarizing filter, respectively.
Figure 1B:
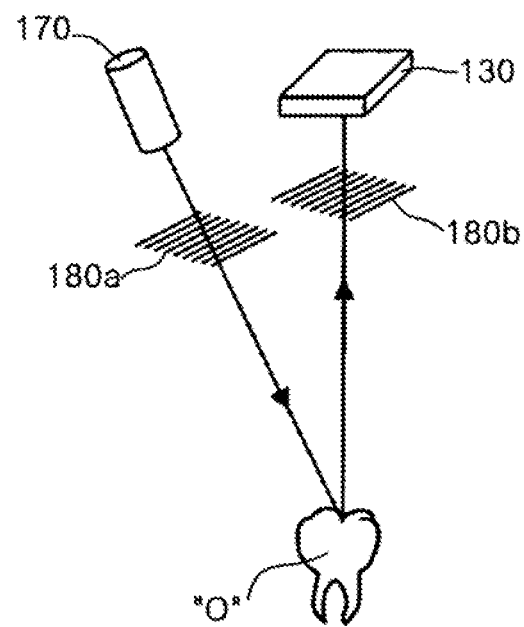

| | |
|---|---|
| 1: 3D scanner | 10: case |
| 11: main body case | 12: lower case |
| 13: upper case | 14: tip case |
| 16: aperture | 18: probe tip mount |
| 20: camera | 21: first imaging lens |
| 22: second imaging lens | 31a and 32a: imaging board |
| 31b, 32b: imaging sensor | 41, 42: light path changing mirror |
| 50: camera mount | 51, 52: incident light path |
| 53: projection light path | 60: light path changing member |
| 70: light projector | 80: polarizing filter |
| $d_c$: set distance | $\delta$: set angle |

DETAILED DESCRIPTION

Hereinafter, some embodiments of the present disclosure will be described in detail with reference to illustrative drawings. In adding reference numerals to components of each drawing, it is to be noted that the same components have the same numerals, if possible, even if the components are illustrated on different drawings. In addition, in describing the embodiments of the present disclosure, a detailed description of known configurations or functions related thereto will be omitted when it is determined that the detailed description may hinder understanding of the embodiments of the present disclosure.

In describing components of embodiments of the present disclosure, terms such as first, second, A, B, (a), (b), and the like may be used. These terms are only used to distinguish the components from other components, and the nature, sequence, order, or the like of the corresponding components are not limited by the terms. In addition, unless defined otherwise, all terms used herein, including technical or scientific terms, have the same meaning as commonly understood by a person of ordinary skill in the art to which the present disclosure belongs. Terms such as those defined in a commonly used dictionary should be interpreted as having a meaning consistent with the meaning in the context of the related art, and unless explicitly defined in the present application, the terms should not be interpreted in an ideal or overly formal sense.

In describing the present disclosure, a 3D scanner 1 may refer to a device that scans an object to obtain image data representing the object and obtains a 3D digital model of the object based on the image data. As an example, the 3D scanner 1 may be a table-type scanner configured to place an object on a tray and obtain a 3D model of the object according to rotation and tilting of the tray, or a handheld-type scanner configured to execute a scanning process and obtain a 3D model of an object when held and directed toward the object by a user. In describing the present disclosure, the accompanying drawings illustrate a handheld-type scanner as an example, but the present disclosure is not necessarily limited thereto.

Figure 2:
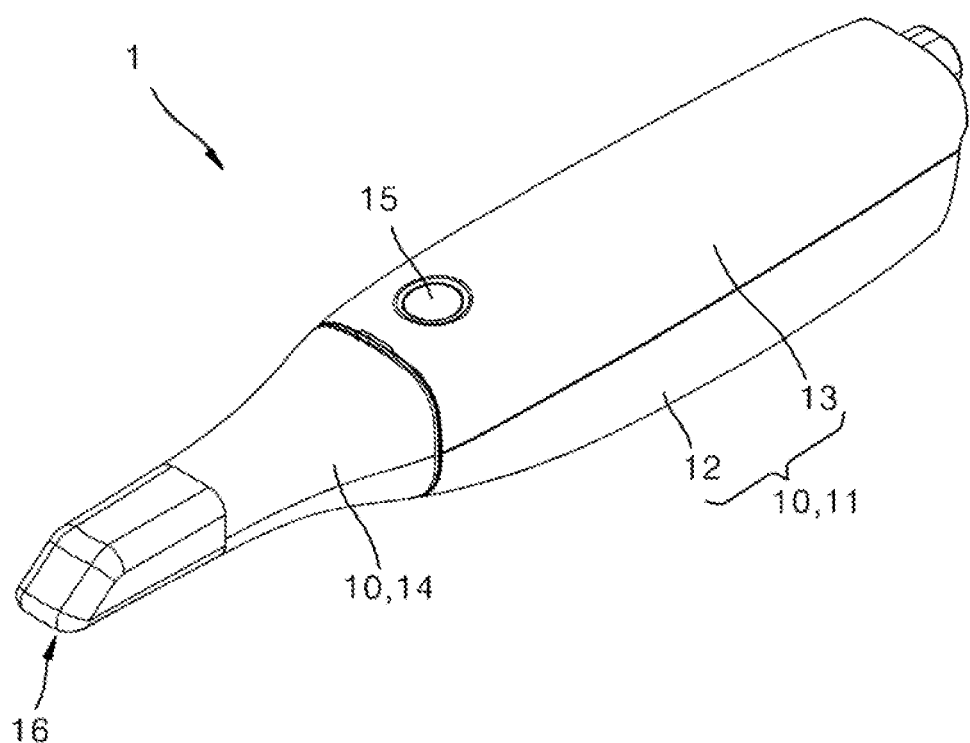
FIG. 2 is a perspective view illustrating an embodiment of a 3D scanner according to the present disclosure.
Figure 3:
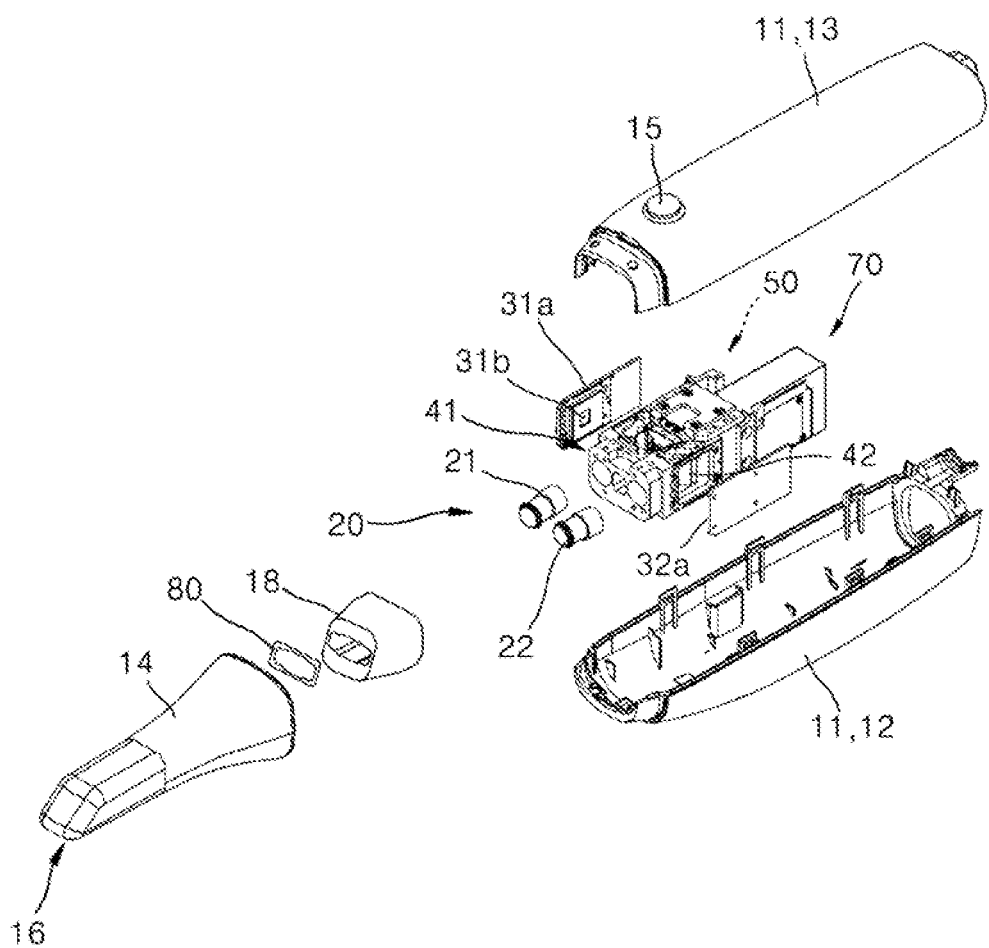
FIG. 3 is an exploded perspective view of FIG. 2.
Figure 4:
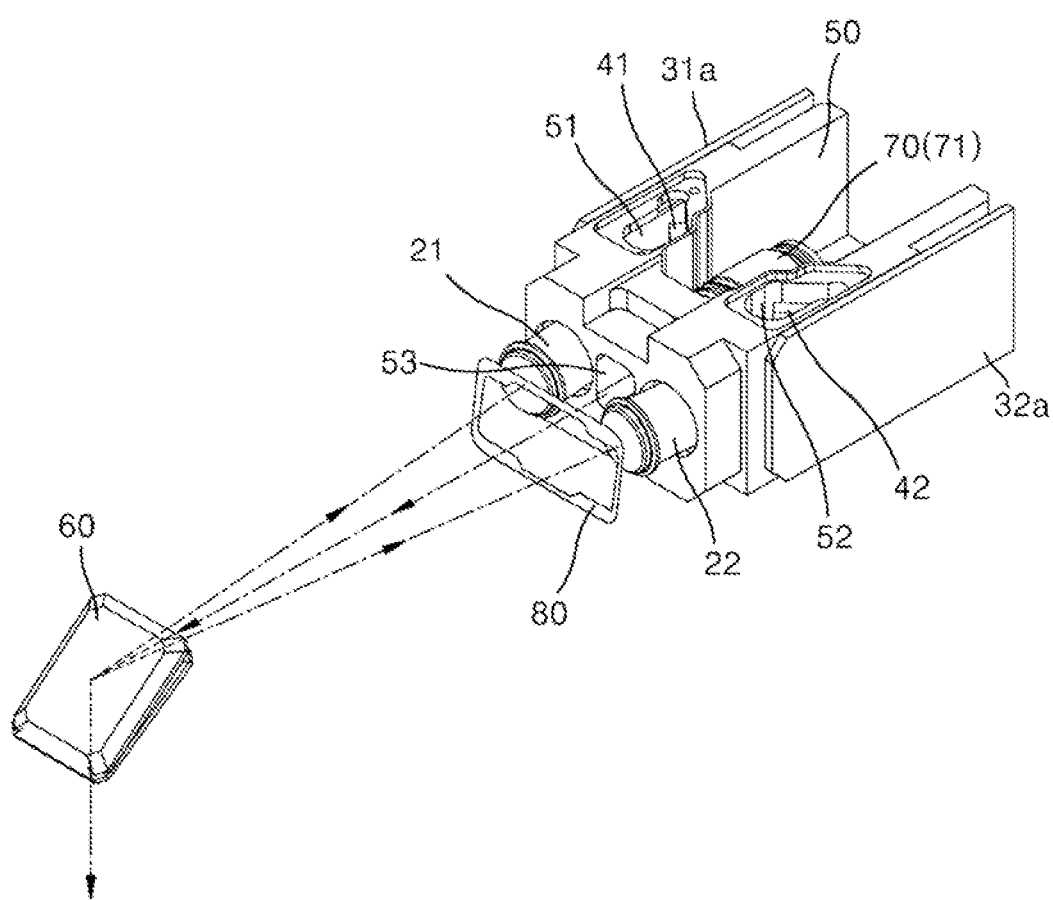
FIG. 4 is a view illustrating an arrangement relationship of a camera, a polarizing filter, and a light path changing member.
Figure 5:
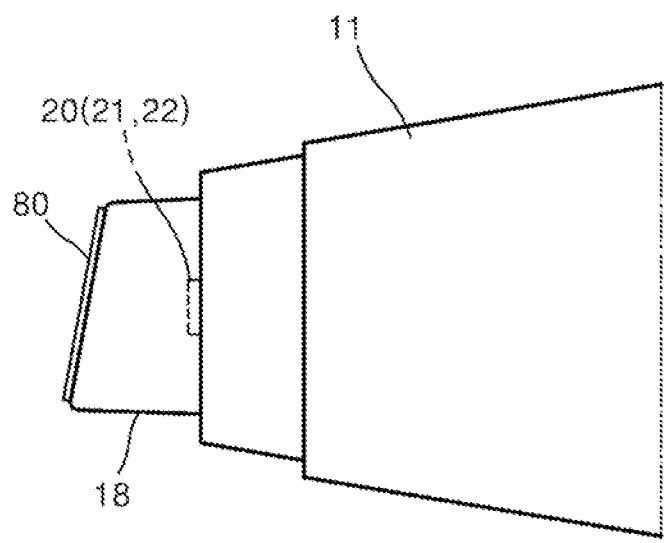
FIG. 5 is a side view illustrating a portion of the 3D scanner according to the present disclosure.

FIG. 2 is a perspective view illustrating an embodiment of a 3D scanner 1 according to the present disclosure, FIG. 3 is an exploded perspective view of FIG. 2, FIG. 4 is a view illustrating an arrangement relationship of cameras 20, a polarizing filter 80, and a light path changing member 60, and FIG. 5 is a side view illustrating a portion of the 3D scanner 1 according to the present disclosure.

Referring to FIGS. 2 to 5, an embodiment of the 3D scanner 1 according to the present disclosure includes a case 10 that can be put into and taken out of an oral cavity.

A camera 20 may be disposed inside the case 10. The camera 20 may receive light incident into the case 10. Although not illustrated in the drawings, the camera 20 may be a single camera 20 and may be disposed inside the case 10. In addition, the camera 20 may be a pair of stereo cameras 20 and may be disposed inside the case 10 as illustrated in FIG. 3.

In this case, when the pair of stereo cameras 20 is disposed, the cameras may be disposed apart from each other in the width direction of the case 10 to cause light incident from one end of the case 10 to pass through different paths. Hereinafter, for convenience of description, it is assumed that the cameras 20 are disposed inside the case 10, but it is to be noted that application of a single camera 20 is not completely excluded.

Here, the term "light" means, in a broad sense, light in the visible ray region that can be recognized by the human eye, but may be a concept including all light in the infrared or ultraviolet region that can be observed by using a special optical device. In a narrow sense, the light may refer to a form of an object to be measured. In this case, the object to be measured by the 3D scanner 1 according to the present disclosure may include inside of a patient's actual oral cavity, an impression model by taking an impression of the patient's oral cavity, and a plaster model obtained by adding a solidifying material (e.g., plaster) in the impression model.

Accordingly, the case 10 may be provided with an aperture 16 opened such that an image of the object is introduced into the inside thereof in the form of light through one end. The aperture 16 may be an entrance through which light outside the case 10 is introduced into the case 10. Light incident through the aperture 16 is transmitted to each of the stereo cameras 20 while forming different light paths. Light passing through the stereo cameras 20 is received by the 3D scanner 1 through imaging sensors 31b and 32b provided on imaging boards 31a and 32a, which will be described later, and an image can be obtained.

Here, since images can be obtained as a plurality of image data at the same time, it is possible to obtain 3D data corresponding to the image data when the separation distance between the pair of stereo cameras 20 and the focal length of a target point photographed through each of the stereo cameras 20 are known.

Although not specifically illustrated, the cameras 20 may include at least one imaging lens capable of focusing on an intraoral image. As an example, the cameras 20 may include a plurality of the imaging lenses 21 and 22 and may further include the imaging boards 31a and 32a having the imaging sensors 31b and 32b which correspond to the imaging lenses 21 and 22, respectively. In addition, an embodiment of the 3D scanner 1 according to the present disclosure may further include a camera control board equipped with electrical components for controlling operations of the pair of stereo cameras 20 and a scanning control board equipped with electrical components for processing scanned images.

As illustrated in FIG. 3, the case 10 serves to provide a predetermined space such that the above-described pair of the stereo cameras 20, imaging boards 31a and 32a, camera control board (not illustrated), and scanning control board (not illustrated) are embedded therein.

More specifically, as illustrated in FIG. 2, the case 10 includes a main body case 11 that includes a lower case 12 in which a predetermined space in which the above-mentioned components are embedded is formed, and an upper case 13 provided on an upper side of the lower case 12 and detachably coupled to the lower case 12 to cover the above-mentioned components.

In addition, the case 10 may further include a tip case 14 which is detachably coupled to one end of the main body case 11 and where the above-described aperture 16 is formed therein, thereby guiding light incident into the main body case 11 through the aperture 16 and light projected from the inside of the main body case 11 through the aperture 16.

Here, the light incident into the main body case 11 through the aperture 16 (hereinafter, referred to as "incident light") refers to an image which is a form of an object, and the light projected from the inside of the main body case 11 through the aperture 16 (hereinafter, referred to as "projection light") refers to emission light emitted from a light projector 70 to be described later.

In the inside of the tip case 14, a light guiding structure through which the incident light and the projection light are easily emitted to inside and outside of the case 10 may be provided. As an example, the aperture 1δ may be open in one direction orthogonal to the longitudinal direction of the tip case 14. However, the aperture 16 is open in one direction orthogonal to the longitudinal direction of the tip case 14 for convenience in the configuration of the 3D scanner 1 according to the present disclosure, and the aperture 16 need not necessarily be orthogonal to the longitudinal direction of the tip case 14. That is, the aperture 1δ may have a normal vector parallel to the longitudinal direction of the tip case 14 or may have a normal vector inclined at a predetermined angle.

In addition, the light path changing member 60 to be described below may be disposed inside the tip case 14. The light path changing member 60 may guide light incident from the aperture 16 to the polarizing filter 80 described below. The light path changing member 60 may be disposed at a position corresponding to the position of the aperture 16. In addition, the light path changing member 60 may be provided on an inner surface of the tip case 14 in order to miniaturize the tip case 14. The light path changing member 60 may be a reflective mirror or a prism, but is not limited to the listed examples.

As described above, the front ends of the cameras 20 may be disposed to be enclosed by the tip case 14, and may be arranged to be inserted in the tip case 14 by a predetermined distance. In addition, the rear ends of the cameras 20 may be provided to be connected to a camera mount 50 fixed inside the main body case 11.

However, as illustrated in FIG. 3, an embodiment of the 3D scanner 1 according to the present disclosure may further include the light projector 70 disposed on one side of the cameras 20 inside the case 10 to emit predetermined light (i.e., projection light), while emitting the projection light to an object through the aperture 16 formed at the front end of the tip case 14 of the case 10.

An embodiment of the 3D scanner 1 according to the present disclosure proposes an optimal layout structure, which, while allowing the above-described components to be placed inside the case 10, enables, from a user's point of view, to manufacture the main body case 11 to be slim such that the 3D scanner 1 according to the present disclosure can be easily gripped and used and enables, from a patient's point of view, the tip case 14 to be fabricated as long and slim as possible so that the tip case can be easily put into and taken out of an oral cavity (or so that the user can easily direct the tip case toward an object). As an example, the main body case 11 may be configured such that the light projector 70 and the cameras 20 are disposed therein.

As will be described later, the slim design of the main body case 11 is related to the arrangement design of the imaging sensors 31b and 32b separately provided for each incident light incident through each of the cameras 20, while the slim design of the tip case 14 is also related to the arrangement design of the polarizing filter 80.

Hereinafter, the slim design method of the main body case 11 will be described in more detail.

As illustrated in FIGS. 3 and 4, inside the case 10, one ends of the cameras 20 may be provided to protrude toward the tip case 14, the other ends of the cameras 20 are inserted and installed, and a camera mount 50 forming an optical waveguide as a path for incident light transmitted through the cameras 20 or projection light emitted from the light projector 70 may be disposed. The optical waveguide formed in the camera mount 50 may be provided in a form of a dark room so that the incident light incident from the aperture 16 and the projection light emitted from the light projector 70 are mutually separated from each other and do not affect each other.

That is, the optical waveguide may include a projection light path 53 which provides a light path for the projection light emitted from the light projection lens 71 of the light projector 70 to the tip case 14, one side incident light path 51 which provides a light path for incident light incident through a first imaging lens 21, and another incident light path 52 providing a light path for incident light incident through a second imaging lens 22. Here, the projection light path, the one side incident light path 51, and the other side incident light path 52 may be provided to be mutually separated from one another, so that the light of each path does not affect the light of the other paths.

In addition, the light projector 70 is located at the center of the other end of the pair of stereo cameras 20 arranged at a predetermined distance from each other in the width direction of the case 10, so that the projection light path 53 may be provided between the one side incident light path 51 and the other side incident light path 52. As an example, the cameras 20 may include the first imaging lens 21 disposed on one side of the light projector 70 and the second imaging lens 22 disposed on the other side of the light projector 70 and opposite to the first imaging lens 21, thereby constituting a pair of stereo cameras 20.

The one side incident light path 51 and the other side incident light path 52 may be provided to coincide with the longitudinal directions of the corresponding imaging lenses 21 and 22, respectively, so that the incident light incident from the cameras 20 is transmitted therethrough, and may respectively be open to one side and the other side of the camera mount 50.

Here, the imaging boards 31a and 32a in which the imaging sensors 31b and 32b are integrated may be arranged vertically to be in close contact with one side wall and the other side wall in the width direction of the case 10. More specifically, the one side imaging board 31a may be disposed to be in close contact with one side surface of the camera mount 50 and may be disposed between one side wall of the case 10 in the width direction. In addition, the other side imaging board 32a may be disposed to be in close contact with the other side surface of the camera mount 50 and may be disposed between the other side wall of the case 10 in the width direction. In this case, the one side imaging board 31a may be provided such that the imaging sensor 31b integrated therein is exposed to the one side incident light path 51, and the other side imaging board 32a may be provided such that the imaging sensor 32b integrated therein is exposed to the other side incident light path 52.

Meanwhile, an embodiment of the 3D scanner 1 according to the present disclosure may further include a pair of light path changing mirrors 41 and 42 disposed to change the light paths of incident light passing through each of the imaging lenses 21 and 22 toward the imaging sensors 31b and 32b integrated in the imaging boards 31a and 32a. One of the pair of light path changing mirrors 41 and 42 may be one side light path changing mirror 41 that changes a path of incident light such that the incident light transmitted through the one side incident light path 51 is emitted to the imaging sensor 31b integrated in the one side imaging board 31a, and the other of the pair of light path changing mirrors 41 and 42 may be the other side light path changing mirror 42 that changes a path of incident light such that the incident light transmitted through the other side incident light path 52 is emitted to the imaging sensor 32b integrated in the other side imaging board 32a.

Here, the pair of light path changing mirrors 41 and 42 may include reflection mirrors capable of reflecting light. However, the light path changing mirrors are not necessarily limited to only the reflective mirrors, and may include other optical elements capable of reflecting light.

An embodiment of the 3D scanner 1 according to the present disclosure has a main technical substance of obtaining a 3D model of the shape (i.e., an image) of an object by using the cameras 20.

However, as described above, one ends of the pair of stereo cameras 20 (in the direction in which the tip case 14 is provided in the drawing) are each disposed to be in an angle facing the one light path changing member 60, which is provided in the aperture 16, while the other ends of the pair of stereo cameras 20 (in the direction in which the light projector 70 is provided in the drawing) should have a configuration in which incident light passing through each of the other ends is passing in a linear direction.

Accordingly, the pair of imaging boards 31a and 32a should be disposed apart from each other in the width direction of the case 10 to be orthogonal to the linear direction of the other end of each of the pair of stereo cameras 20. However, in this case, there is a possibility that the thickness of the main body case 11 in the width direction may be increased due to the lengths of the pair of imaging boards 31a and 32a.

As described above, in an embodiment of the 3D scanner 1 according to the present disclosure, the incident light paths 51 and 52 are open toward the one side and the other side of the camera mount 50, respectively, the imaging boards 31a and 32a are vertically arranged between the one side surface and the other side surface of the camera mount 50 and the one side wall and the other side wall of the case 10, respectively, and the pair of light path changing mirrors 41 and 42 disposed to change the light paths of incident light transmitted through the pair of stereo cameras 20 are provided. As a result, it is possible to form the main body case 11 to be slim so that a measurer can easily grip and use the main body case 11 with only his/her thumb, forefinger, and middle finger.

The pair of light path changing mirrors 41 and 42 may be disposed to have reflector surfaces having an angle that causes incident light transmitted through the cameras 20 to be incident on one surface of each of the imaging sensors 31b and 32b provided on the pair of imaging boards 31a and 32a at right angles.

To this end, the pair of light path changing mirrors 41 and 42 may be disposed such that the reflector surfaces are inclined with respect to the longitudinal direction of the case 10. That is, the one side light path changing mirror 41 may be provided such that incident light transmitted through the first imaging lens 21 is incident through the one side incident light path 51 and is then reflected by the reflector surface of the one side light path changing mirror 41 to be transmitted to the imaging sensors 31b of the one side imaging board 31a. Similarly, the other side light path changing mirror 42 may be provided such that incident light transmitted through the second imaging lens 22 is incident through the other side incident light path 52 and is then reflected by the reflector surface of the other side light path changing mirror 42 to be transmitted to the imaging sensors 32b of the other side imaging board 32a.

Hereinafter, the polarizing filter 80, which is one of the components of the 3D scanner 1 according to the present disclosure, will be described in detail.

Referring to FIG. 3, the 3D scanner 1 according to the present disclosure may include the polarizing filter 80. The polarizing filter 80 may be disposed inside the case 10 to polarize light introduced into the 3D scanner 1. As an example, the polarizing filter 80 may be disposed apart from front lenses of the cameras 20 by a predetermined set distance dc. The polarizing filter 80 is capable of preventing light reflected from the inside of the object O from being received by the lenses of the cameras 20 when light entering the inside from the outside of the 3D scanner 1 (i.e., incident light) is received by the lenses of the cameras 20. Accordingly, there are advantages in that the user is able to obtain clear image data representing the object by using the 3D scanner 1 and obtain an accurate 3D model.

Meanwhile, apart from the fact that the polarizing filter 80 polarizes light entering from the outside, when the projection light generated by the light projector 70 is emitted to the outside of the 3D scanner 1 and does not illuminate the object, a problem arises in that clear image data cannot be obtained. As an example, at least some of the projection light emitted by the light projector 70 may pass through the polarizing filter 80 to be emitted to the outside of the 3D scanner 1, but some of the remainder of the projection light may be reflected from the surface of the polarizing filter 80. When the light reflected from the surface of the polarizing filter 80 directly enters the imaging lenses 21 and 22 of the cameras 20, the light may be mixed with light representing the object, and the image data obtained through the imaging sensors 31b and 32b may include a so-called "ghost image" or noise in which an image point that is brighter than the surrounding image is generated by the projection light emitted from the light projector 70.

In order to solve these problems, the polarizing filter 80 may be disposed to be inclined in one direction by a predetermined set angle δ. More specifically, the polarizing filter 80 may be disposed to be inclined by a predetermined set angle δ with respect to a first imaginary plane C1 perpendicular to the path of light emitted by the light projector 70 (more precisely, the projection light path).

Figure 6:
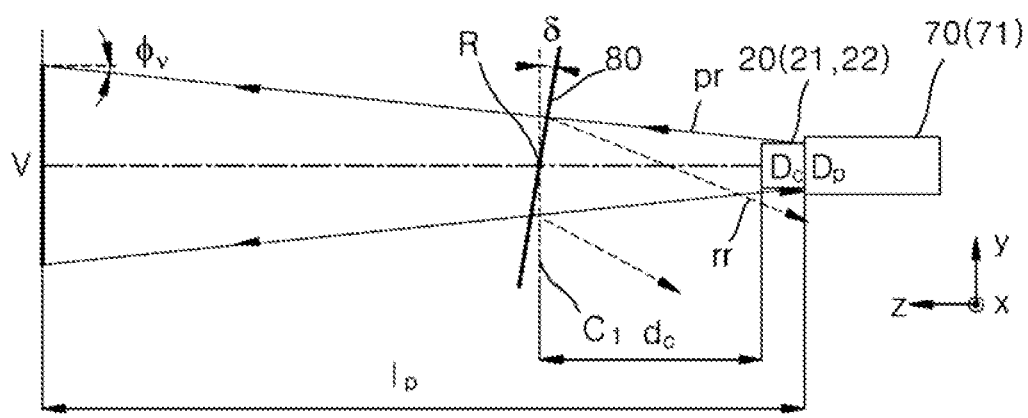
FIG. 6 is a schematic view illustrating a process in which some of light generated from a light projector travels toward a camera, when viewed from a side.
Figure 7:
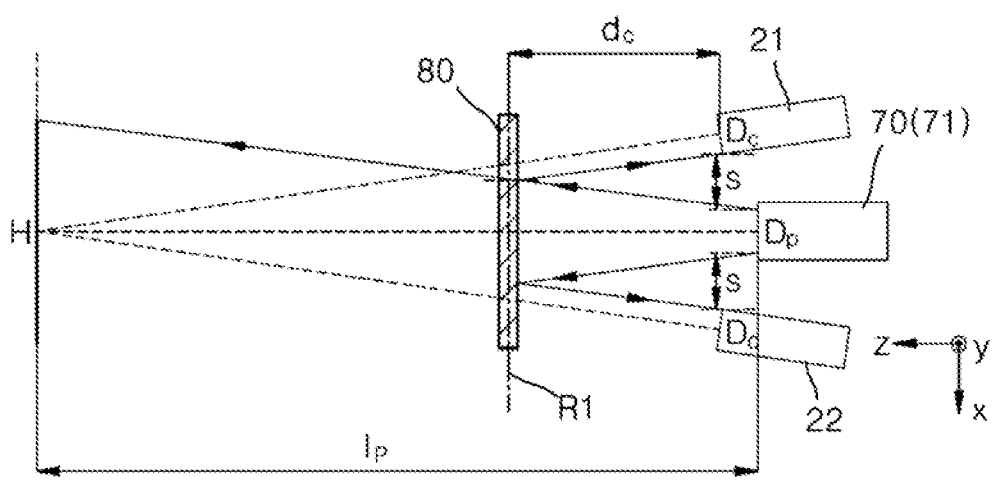
FIG. 7 is a schematic view obtained when
Figure 8:
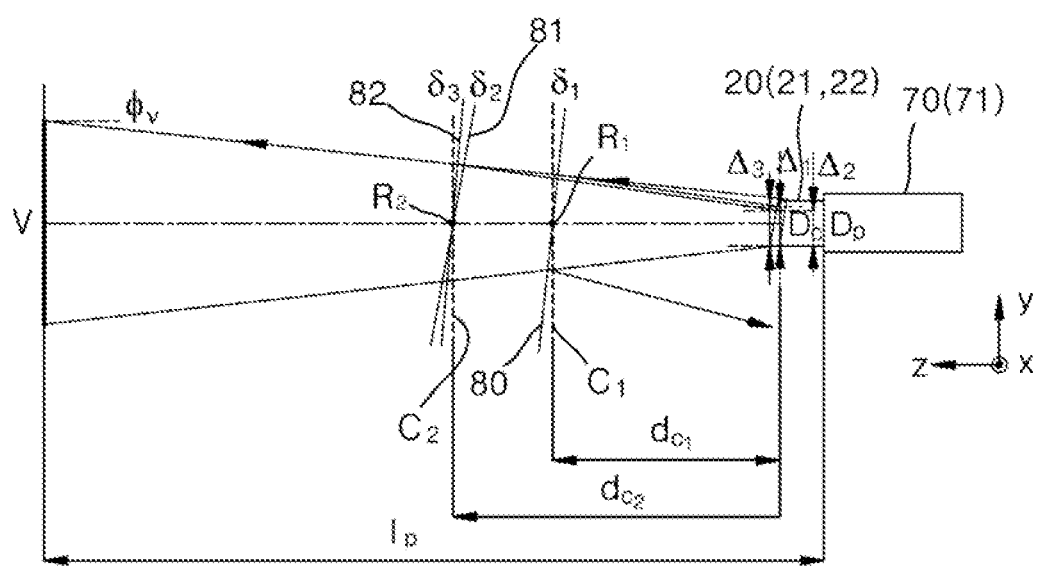
FIG. 8 is a schematic view illustrating a process in which an angle of a polarizing filter changes depending on a set distance between the polarizing filter and the camera.
Figure 9:
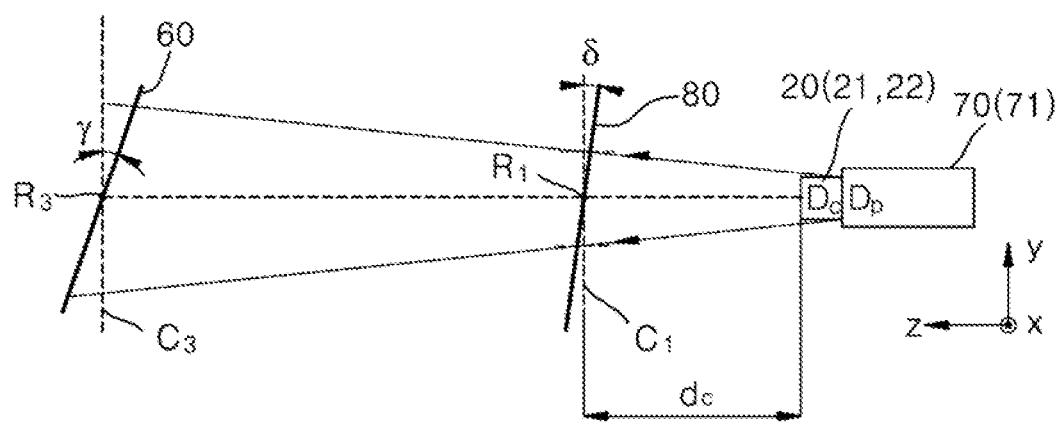
FIG. 9 is a schematic view illustrating the angle of a polarizing filter depending on an angle of a light path changing member.

FIG. 6 is a schematic view illustrating a process in which some of light generated from the light projector 70 travels toward the cameras 20, as viewed from a side, FIG. 7 is a schematic view obtained when FIG. 6 is viewed from top, and FIG. 8 is a schematic view illustrating a process in which the set angle δ of the polarizing filter 80 changes depending on the set distance between the polarizing filter 80 and the cameras 20.

Referring to FIG. 6, the projection light pr generated from the light projector 70 reaches one surface of the polarizing filter 80 (which may refer to an inner surface in view of the structure of the 3D scanner 1 according to the present disclosure), and the projection light pr is reflected with reference to the normal line of the one surface of the polarizing filter 80 according to the law of reflection. The reflection light rr reflected from the one surface of the polarizing filter 80 leaves the lenses of the cameras 20 and travels to the outside. That is, since the polarizing filter 80 is disposed to be inclined by the predetermined set angle δ in one direction, at least some of the projection light pr emitted by the light projector 70 passes through the polarizing filter 80 to be transmitted to the outside of the 3D scanner 1 and to illuminate the object. In addition, some of the remainder of the projection light pr emitted by the light projector 70 is reflected from the surface of the polarizing filter 80 to be turned into reflection light rr, and the reflection light rr travels to the outside of the lenses of the cameras 20 and is not received by the cameras 20. As a result, the projection light pr generated from the light projector 70 is immediately received by the lenses of the cameras 20 to prevent a ghost image from being generated, and the user is able to obtain clear image data representing the object through incident light refracted from another surface to one surface and received by the cameras 20. In addition, some of another remainder of the projection light pr emitted by the light projector 70 may be absorbed by the polarizing filter 80.

That is, the projection light may travel in various ways. For example, some of the light that encounters the polarizing filter 80 is transmitted through the polarizing filter 80, some of the remainder is reflected from the surface of the polarizing filter 80, and some of another remainder is absorbed by the polarizing filter 80.

Meanwhile, the above-mentioned setting angle δ may be set to satisfy the conditions of the following equation.

$$|\tan\delta| \geq \frac{\left(\frac{D_c}{2d_c} + \frac{V}{2l_p}\right)}{\left(1 - \frac{D_c V}{4d_c l_p}\right)} \quad \text{[Equation 1]}$$

Here, δ may be a set angle which is an inclination angle when the polarizing filter 80 is disposed to be inclined, dc may be a set distance between the polarizing filter 80 and the front lenses of the cameras 20 (i.e., the imaging lenses), Dc may be a lens aperture (an effective diameter) of the cameras 20, lp may be a distance from the light projection lens 71 of the light projector 70 to an object (i.e., the distance to the projection surface on which the object exists), and V may be a vertical length of the projection surface.

For example, the set angle δ may be greater than or equal to 10° and less than or equal to 90°, or greater than or equal to −90° and less than −10°. That is, the polarizing filter 80 may be disposed to be inclined clockwise or counterclockwise in the schematic view illustrated in FIG. 6. Because the set angle δ of the polarizing filter 80 is determined according to the above-mentioned range conditions, the reflection light rr generated as the light emitted from the light projector 70 is reflected by the polarizing filter 80 travels to the outside of the lenses of the cameras 20, so that creation of a ghost image can be prevented.

Meanwhile, referring to FIGS. 3, 4, 6, and 7, the polarizing filter 80 may be disposed to be inclined by the set angle δ around a predetermined rotation axis. For example, the predetermined rotation axis may be a first rotation axis RI that is parallel to the illustrated x-axis and is included in a first plane C1. That is, the polarizing filter 80 may be substantially inclined clockwise or counterclockwise by the set angle δ around the first rotation axis C1 in the yz plane. In addition, some of the light emitted from the light projection lens 71 of the light projector 70 may be reflected from the surface of the polarizing filter 80 and may travel toward the first imaging lens 21 and the second imaging lens 22. For example, when the light reflected from the surface of the polarizing filter 80 travels toward a lower side of the first imaging lens 21 and a lower side of the second imaging lens 22, the x-axis horizontal separation distance between the light projection lens 71 and the light traveling toward the first imaging lens 21 and the x-axis horizontal separation distance between the light projection lens 71 and the light traveling toward the second imaging lens 22 may be equal to each other.

In addition, the shortest distance s between the imaging lenses 21 and 22 of the cameras 20 and the light projection lens 71 of the light projector 70 may be greater than the x-axis horizontal distance by which the outermost ray of the light emitted from the light projector 70 travels after being reflected by the polarizing filter 80. In this case, the projection light generated from the light projector 70 can stably travel out of the lenses of the cameras 20, and generation of a ghost image can be prevented more reliably.

Meanwhile, when the polarizing filter 80 is disposed between the aperture 16 and the light path changing member 60, the set distance between the polarizing filter 80 and the imaging lenses 21 and 22 of the cameras 20 may be excessively increased, and scratches formed on an end surface of the polarizing filter 80, foreign matter attached to the end surface of the polarizing filter 80, and the like may appear in an image obtained by the cameras 20. Accordingly, the polarizing filter 80 may be disposed inside the tip case 14 between the light path changing member 60 and the cameras 20.

In addition, referring to FIG. 8, the polarizing filter 80 is disposed to be inclined by a predetermined critical angle or more, and a size of the critical angle may be decreased as the set distance dc is increased. For the description of the above-described characteristics, it is assumed that the polarizing filter 80 is disposed to have an arbitrary first set angle δ1 at a first set distance dc1. When the polarizing filter 80 is disposed to be inclined by the first set angle δ1, the outermost ray (more precisely, the ray emitted from the uppermost end of the light projection lens 71) of the projection light pr emitted by the light projector 70 may be reflected from the surface of the polarizing filter 80. The outermost ray reflected from the surface of the polarizing filter 80 may be received in at a first position Δ1 of the imaging lenses 21 and 22 of the cameras 20. In order to prevent the reflection light reflected from the surface of the polarizing filter 80 from generating a ghost image by traveling to the outside of the imaging lenses 21 and 22 of the cameras 20, the first position Δ1 should be equal to or less than 0. The first set angle δ1 at which the first position Δ1 becomes 0 is called a first critical set angle.

Meanwhile, when the set distance of the polarizing filter 80 is increased to a second set distance dc2 greater than the first set distance dc1 and the set angle δ of the polarizing filter 80 is set to a second set angle δ2 that is equal to the first set angle δ1, the traveling distance of the reflection light reflected from the surface of the polarizing filter 80 will be increased. Therefore, even when the set angle δ of the polarizing filter 80 is set to be smaller than the first set angle δ1, the reflection light reflected from the surface of the polarizing filter 80 may be received at a second position Δ2 of the imaging lenses 21 and 22 smaller than the first position Δ1. Therefore, when the set distance of the polarizing filter 80 is the second set distance dc2, the set angle δ may be set to a third set angle δ3, which is smaller than the second set angle δ2, or more, and the third position Δ3 of the outermost light ray may be larger than the second position Δ2 of the outermost ray. Accordingly, when the set distance dc, which is the distance between the cameras 20 and the polarizing filter 80, is increased, the critical set angle is decreased. That is, the critical set angle of the polarizing filter 80 for preventing a ghost image at the second setting distance dc2 may be smaller than the critical set angle of the polarizing filter 80 for preventing a ghost image at the first set distance dc1.

In addition, the light path changing member 60 may guide the light incident through the aperture 16 to the polarizing filter 80 and the cameras 20, and the angle γ of the light path changing member 60 may be greater than or equal to 0° and less than or equal to 90°. In this case, when the polarizing filter 80 is disposed to be inclined by the predetermined critical angle while having a minimum set distance, the polarizing filter 80 may be disposed to have an angle range of −85° to 5° (δ−γ) with respect to the light path changing member 60. That is, since the polarizing filter 80 is disposed to have the above-mentioned angle range with respect to the light path changing member 60, the light path changing member 60 may refract and/or reflect the light incident from the outside to the polarizing filter 80, and the polarizing filter 80 may transmit the incident light reaching the external surface thereof by the light path changing member 60 to be received by the imaging lenses 21 and 22 of the cameras 20.

Hereinafter, the arrangement position of the polarizing filter 80 will be described in detail.

Referring to FIGS. 3 and 5, the 3D scanner 1 according to the present disclosure may further include a probe tip mount 18 protruding by a predetermined thickness from one end of the main body case 11 in which the light projector 70 and the cameras 20 are disposed. The rear end of the probe tip mount 18 may be inserted into the inner space of the main body case 11 and the front end of the probe tip mount 18 may protrude to the front of the main body case 11. The tip case 14 may be mounted on the probe tip mount 18. A rear end of the tip case 14 may be put onto an outer peripheral surface of the probe tip mount 18.

In addition, a light inlet and outlet port may be provided in the probe tip mount 18. The light inlet and outlet port may be provided at the center of the probe tip mount 18 and may define a path through which the light incident into the 3D scanner 1 travels to the cameras 20 and a path through which the projection light generated from the light projector 70 travels to the outside of the 3D scanner 1.

In addition, the polarizing filter 80 may be coupled to one end of the probe tip mount 18. For example, the polarizing filter 80 may be attached to one end of the probe tip mount 18. However, the coupling method is merely an example, and at least one of various coupling means for coupling the polarizing filter 80 to the probe tip mount 18 may be used. One end of the probe tip mount 18 may be inclined such that the polarizing filter 80 has a predetermined set angle δ with respect to the cameras 20. For example, the inclination of one end of the probe tip mount 18 may be the same as the predetermined set angle δ of the polarizing filter 80 with respect to the cameras 20. Accordingly, the probe tip mount 18 enables the polarizing filter 80 to stably maintain the predetermined set angle δ with respect to the cameras 20.

Meanwhile, in some cases, the probe tip mount 18 may further include a rotation member (not illustrated) that serves as the above-described first rotation axis RI and may be coupled to central portions of both sides of the polarizing filter 80 so that the polarizing filter 80 can be rotated.

The polarizing filter 80 may be configured such that one surface thereof is exposed to the outside when the tip case 14 including the aperture 16 is unmounted from the probe tip mount 18 and removed from the main body case 11. That is, the outer surface of the polarizing filter 80 may be exposed to the outside when the tip case 14 is removed. Accordingly, the user may perform maintenance/repair work (e.g., cleaning) on the outer surface of the polarizing filter 80.

More specifically, one surface of the polarizing filter 80 may be entirely exposed to the outside without being covered by the probe tip mount 18. For example, the outer surface of the polarizing filter 80 is not fitted into the probe tip mount 18, and the entire outer surface thereof may be exposed to the outside as the tip case 14 is removed from the main body case 11. Accordingly, there is an advantage in that problems of accumulation of foreign matter between other components and the polarizing filter 80, which may be caused when the polarizing filter 80 is conventionally fitted and coupled to the other components, and consequent difficulty in maintenance/repair, can be solved. In addition, even when the polarizing filter 80 is damaged and does not function, due to the arrangement structure of the polarizing filter 80 of the 3D scanner 1 according to the present disclosure, the damaged polarizing filter 80 can be easily removed and replaced. Accordingly, the maintenance/repair time for the polarizing filter 80 can be reduced, and the 3D scanner 1 according to the present disclosure can be maintained in the best condition for a long period of time.

The probe tip mount 18 may be made of a heat dissipation material to easily dissipate heat inside the main body case 11 to the outside of the main body case 11. The heat dissipation material is preferably an aluminum material. However, the heat dissipation material is not limited to the aluminum material, and may be made of other materials having a heat dissipation function.

The operation of the 3D scanner 1 according to the present disclosure configured as described above will be described in more detail with reference to the accompanying drawings.

The user pushes an operation button 15 provided on the upper portion of the case 10 to measure an object by using an embodiment of the 3D scanner 1 according to the present disclosure. Thereafter, projection light is emitted from the light projector 70. The projection light emitted from the light projector 70 is emitted to the aperture 16 side by sequentially passing through the projection light path 53 of the light waveguide provided in the camera mount 50 and the input/output light path provided in the tip case 14, and the projection light is emitted into the oral cavity of a patient through the aperture 16 by the light path changing member 60.

At the same time, since the cameras 20 are operated by the user pushing the operation button 15, two image data having a certain point of an object as the same focal point may be secured.

At this time, the image data representing the object exists in the form of light by the projection light, is sequentially incident to the inside of the tip case 14 through the aperture 16 contrary to the projection light, is subjected to a change in path by the light path changing member 60, and is incident to the lenses of the cameras, which substantially photograph the reflection surface of the light path changing member 60 via the above-described incident light paths 51 and 52. In addition, image data may be secured by being emitted to the imaging sensors 31*b* and 32*b* of the corresponding imaging boards 31*a* and 32*a* by the respective light path changing mirrors 41 and 42. Based on the image data obtained in this way, a 3D model representing the object can be easily obtained.

The forgoing description is merely an example of the technical idea of the present disclosure, and a person of ordinary skill in the art to which the present disclosure pertains may make various modifications and variations without departing from the essential characteristics of the present disclosure.

Therefore, the embodiments disclosed herein are not intended to limit the scope of the present disclosure, but to describe the technical idea of the present disclosure, and the scope of the technical idea of the present disclosure is not limited by the embodiments. The protection scope of the present disclosure is to be interpreted based on the following claims, and all technical ideas within the scope equivalent thereto are to be construed as being included in the scope of the present disclosure.

INDUSTRIAL APPLICABILITY

The present disclosure provides a 3D scanner that includes a polarizing filter arranged to be spaced apart from the front of the camera by a predetermined distance and inclined by a predetermined angle, thereby preventing a ghost image from being generated and improving the maintenance/repair convenience of the polarizing filter.

What is claimed is:

1. A three-dimensional scanner comprising:
a camera disposed to receive incident light;
a light projector disposed on one side of the camera to emit light to an object; and
a polarizing filter disposed apart from a front surface of the camera by a predetermined set distance,
wherein the polarizing filter is disposed to be inclined by a predetermined set angle with respect to a plane perpendicular to a light path of the light emitted by the light projector,
wherein the set angle satisfies the following equation:

$$|\tan\delta| \geq \frac{\left(\dfrac{D_c}{2d_c} + \dfrac{V}{2l_p}\right)}{\left(1 - \dfrac{D_c V}{4d_c l_p}\right)},$$

wherein $\delta$ is a set angle, $d_c$ is a set distance, $D_c$ is a lens aperture of the camera, $l_p$ is a distance between the light projector and the object, and V is a vertical length of a projection surface,
so that at least some of the light emitted by the light projector passes through the polarizing filter, and some of a remainder of the light is reflected from a surface of the polarizing filter and travels to the outside of a lens of the camera.

2. The three-dimensional scanner of claim 1, wherein the polarizing filter is disposed to be inclined by a predetermined critical angle or more, and a size of the critical angle is decreased as the set distance is increased.

3. The three-dimensional scanner of claim 1, wherein the camera comprises a first imaging lens disposed on one side of the light projector and a second imaging lens disposed on another side of the light projector and opposite to the first imaging lens, and
wherein the polarizing filter is disposed to be inclined by the set angle with respect to a predetermined rotation axis such that horizontal separation distances of some of the light emitted by the light projector reflected from the surface of the polarizing filter and travelling toward each of the first imaging lens and the second imaging lens are equal to each other.

4. The three-dimensional scanner of claim 1, further comprising:
a case formed such that the polarizing filter is disposed therein,
wherein the case comprises:
a main body case in which the light projector and the camera are disposed; and
a tip case in which a light path changing member guiding light incident from an aperture to the polarizing filter is disposed and detachably coupled to the main body case, and
wherein the polarizing filter is disposed between the light path changing member and the camera.

5. The three-dimensional scanner of claim 4, wherein, when the polarizing filter is disposed to be inclined by a predetermined critical angle while having a minimum set distance, the polarizing filter is disposed in an angle range of −85° to 5° with respect to the light path changing member.

6. The three-dimensional scanner of claim 1, further comprising:
a probe tip mount formed to have a predetermined thickness and protrude from one end of a main body case in which the light projector and the camera are disposed,
wherein the polarizing filter is coupled to one end of the probe tip mount, and when a tip case comprising an aperture is detached from the main body case, one surface of the polarizing filter is exposed to outside.

7. The three-dimensional scanner of claim 6, wherein the one surface of the polarizing filter is entirely exposed to the outside without being covered by the probe tip mount.

\* \* \* \* \*